United States Patent [19]

Conrad et al.

[11] 4,294,727

[45] Oct. 13, 1981

[54] PERFUME COMPOSITION CONTAINING 4,5-DIOXA-5-ALKYL-TRICYCLO[7.2.1.0 $^{2,8}$]DODEC-10-ENES AND ITS USE AS AN ODORANT

[75] Inventors: Jens Conrad, Hilden; Horst Upadek, Erkrath; Klaus Bruns, Krefeld-Traar, all of Fed. Rep. of Germany

[73] Assignee: Henkel Kommanditgesellschaft auf Aktien, Dusseldorf-Holthausen, Fed. Rep. of Germany

[21] Appl. No.: 142,607

[22] Filed: Apr. 21, 1980

[30] Foreign Application Priority Data

May 5, 1979 [DE] Fed. Rep. of Germany ....... 2918168

[51] Int. Cl.$^3$ ................................................ C11B 9/00
[52] U.S. Cl. .............................. 252/522 R; 260/340.3
[58] Field of Search ................................... 252/522 R

[56] References Cited

U.S. PATENT DOCUMENTS

4,211,674 7/1980 Lenselink ........................ 252/522 R

FOREIGN PATENT DOCUMENTS

2826302 4/1979 Fed. Rep. of Germany ... 252/522 R

OTHER PUBLICATIONS

Souliers et al., Bull. Soc. Chim. Fr. 1763–1766, 1975.

*Primary Examiner*—John F. Niebling
*Attorney, Agent, or Firm*—Hammond & Littell, Weissenberger and Muserlian

[57] ABSTRACT

This invention is directed to perfume compositions comprising 4,6-dioxa-5-$C_1$-$C_8$-alkyl or $C_2$-$C_8$-alkenyl-tricyclo[7.2.1.0$^{2,8}$]dodec-10-enes, the use of said tricyclododecenes as an odorant, the synthesis of said tricyclododecenes, and novel tricyclododecenes.

5 Claims, No Drawings

PERFUME COMPOSITION CONTAINING 4,5-DIOXA-5-ALKYL-TRICYCLO[7.2.1.0 $^{2,8}$]DODEC-10-ENES AND ITS USE AS AN ODORANT

BACKGROUND OF THE INVENTION

The present invention relates to tricyclododecenes and more particularly to 4,6-dioxa-5-$C_1$-$C_8$-alkyl or $C_2$-$C_8$-alkenyl-tricyclo[7.2.1.0$^{2,8}$]dodec-10-enes; their preparation; perfume compositions containing the same, and a method of imparting pleasant odors to objects with such compositions.

OBJECTS OF THE INVENTION

An object of the present invention is the development of a perfumery composition comprising an effective amount of at least one tricyclododecene of the formula:

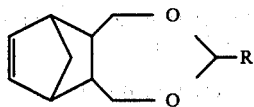

wherein R is a member selected from the group consisting of alkyl having from 1 to 8 carbon atoms, alkenyl having from 2 to 8 carbon atoms and alkynyl having from 2 to 8 carbon atoms, and the remainder customary constituents of perfumery compositions.

Another object of the present invention is the development of a process for the synthesis of the aforesaid tricyclododecene and the use of the same as a perfumery agent.

A further object of the present invention is the obtaining of the novel compounds:
4,6-dioxa-5-ethyl-tricyclo[7.2.1.0$^{2,8}$]dodec-10-ene,
4,6-dioxa-5-propyl-tricyclo[7.2.1.0$^{2,8}$]dodec-10-ene, and
4,6-dioxa-5-isopropyl-tricyclo[7.2.1.0$^{2,8}$]dodec-10-ene.

These and other objects of the invention will become more apparent as the description thereof proceeds.

DESCRIPTION OF THE INVENTION

We have found that 4,5-dioxa-5-aliphatic substituted-tricyclo[7.2.1.0$^{2,8}$]dodec-10-enes of the general formula:

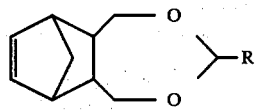

in which R represents a saturated or unsaturated, straight-chain or branched, aliphatic hydrocarbon radical with 1 to 8 carbon atoms, can be used advantageously as fragrances in compositions for the scenting of cosmetics and technical preparations.

More particularly, therefore, the invention relates to a perfumery composition comprising an effective amount of at least one tricyclododecene of the formula:

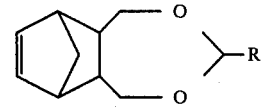

wherein R is a member selected from the group consisting of alkyl having from 1 to 8 carbon atoms, alkenyl having from 2 to 8 carbon atoms and alkynyl having from 2 to 8 carbon atoms, and the remainder customary constituents of perfumery compositions.

Of special interest with respect to perfuming is 4,6-dioxa-5-isopropyl-tricyclo[7.2.1.0$^{2,8}$]dodec-10-ene.

The preparation of one of the products to be used according to the invention was already described by Souliers et al in Bull. Soc. Chim. Fr. 1975, 1763–66, without recognizing olfactory properties of the compound. According to the following reaction scheme, the authors prepared the respective Diels-Alder adducts from cyclopentadiene and maleic acid derivatives. The reduction of the Diels-Alder adducts with lithium aluminum hydride yields the diols, which are turned into dioxepans by ring closure on acetalization with aldehydes.

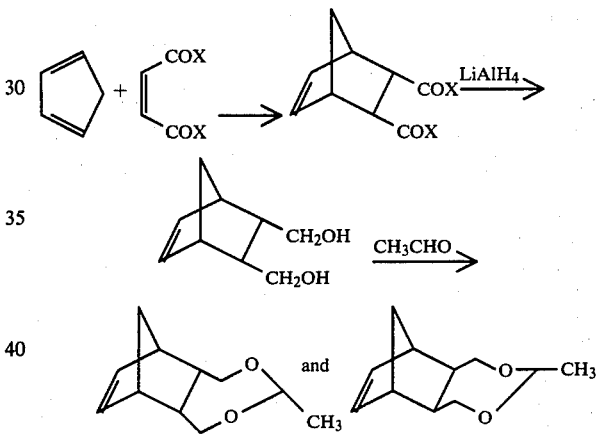

However, the preparation of 4,6-dioxa-5-methyltricyclo[7.2.1.0$^{2,8}$]dodec-10-ene described in the literature as mentioned above, is not feasible for a technical preparation. The technical preparation of the 4,6-dioxa-5-aliphatic substituted-tricyclo[7.2.1.0$^{2,8}$]dodec-10-enes to be used according to the invention requires the skipping of the reduction step indicated above, which results in the diols in a satisfactory manner only when employing lithium aluminum hydride which necessitates special safety measures.

We have now found a technically feasible process by which the 4,6-dioxa-5-aliphatic substituted tricyclo[7.2.1.0$^{2,8}$]dodec-10-enes to be used according to the invention are easily accessible in two reaction steps. In the first reaction step (a), the 1,3-dioxa-2-aliphatic substituted-cyclohept-5-enes needed for the adduct formation are prepared according to conventional methods of organic chemistry by the acetalization of cis-2-buten-1,4-diol with aliphatic aldehydes. In the second step of the process (b), the dioxepine obtained according to (a) is reacted with cyclopentadiene, preferably in the form of the dimer which forms cyclopentadiene "in situ" at reaction temperatures above 150° C. to about 250° C., to form the desired compound. The addition of dicyclopentadiene to the dioxepine at a reaction temperature of about 200° C. is recommended. After distillation, the product usually is obtained as mixture of the four possible stereoisomers and is used as fragrance without further separation. The reaction proceeds according to the following reaction scheme:

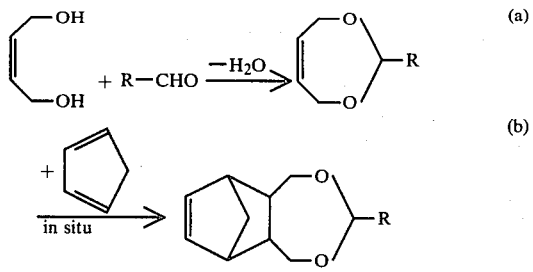

The aldehyde R-CHO can be an alkanal having from 2 to 9 carbon atoms, such as acetaldehyde, propanal, butanal, isobutanal, pentanal, hexanal, heptanal, octanal; or an alkenal having from 3 to 9 carbon atoms, such as acrolein; or an alkynal having from 3 to 9 carbon atoms such as propynal.

Of the products to be used according to the invention and having the general formula, the 4,6-dioxa-6-methyl-tricyclo[7.2.1.0$^{2,8}$]dodec-10-ene has been known from the literature without its suitability as fragrance having been recognized, however. The considerably more interesting compounds in which the alkyl radical R stands for the ethyl, propyl and particularly the isopropyl radical, represent new compounds.

As compounds to be used according to the invention can be mentioned:
4,6-dioxa-5-methyl-tricyclo[7.2.1.0$^{2,8}$]dodec-10-ene
4,6-dioxa-5-ethyl-tricyclo[7.2.1.0$^{2,8}$]dodec-10-ene
4,6-dioxa-5-propyl-tricyclo[7.2.1.0$^{2,8}$]dodec-10-ene
4,6-dioxa-5-isopropyl-tricyclo[7.2.1.0$^{2,8}$]dodec-10-ene
4,6-dioxa-5-butyl-tricyclo[7.2.1.0$^{2,8}$]dodec-10-ene
4,6-dioxa-5-hexyl-tricyclo[7.2.1.0$^{2,8}$]dodec-10ene
4,6-dioxa-5-heptyl-tricyclo[7.2.1.0$^{2,8}$]dodec-10-ene.

The 4,5-dioxa-5-aliphatic substituted-tricyclo[7.2.1.0$^{2,8}$]dodec-10-enes employed according to the invention are valuable fragrances with characteristic perfume notes. They are easily combined into novel and interesting nuances of fragrances. 4,6-Dioxa-5-isopropyl-tricyclo[7.2.1.0$^{2,8}$]dodec-10-ene with its fruity, mushroomlike citrus-jasmone note is the most important of the products since this is especially suitable for the development of novel fragrance compositions.

The 4,6-dioxa-5-aliphatic substituted-tricyclo[7.2.1.0$^{2,8}$]dodec-10-enes to be used according to the invention can be mixed with other fragrances in the most varied ratios to form new fragrance compositions. In general, the content of the 4,6-dioxa-5-aliphatic substituted-tricyclo[7.2.1.0]dodec-10-enes in the fragrance compositions will range from 1% to 50% by weight, based on the total composition. Such compositions can be used for the scenting of cosmetics, such as cremes, lotions, aerosols, toilet soaps, technical compositions, such as washing and cleaning agent compositions, disinfectants and compositions for the treatment of textiles.

The following examples explain the subject matter of the invention in more detail, without being limitative however.

EXAMPLES

First, the preparation of the 4,6-dioxa-5-alkyl-tricyclo[7.2.1.0$^{2,8}$]dodec-10-enes to be used according to the invention is described, which compounds are mixtures of stereoisomer forms, as explained above.

EXAMPLE 1

Preparation of
4,6-dioxa-5-isopropyl-tricyclo[7.2.1.0$^{2,8}$]dodec-10-ene (a) Preparation of
1,3-dioxa-2-isopropyl-cyclohept-5-ene A mixture of 352 gm (4 mols) of cis-2-buten-1,4-diol, 288 gm (4 mols) of isobutyraldehyde, 3.5 gm of p-toluenesulfonic acid and 150 ml of toluene was boiled for one hour employing a water separator. 72 ml of water were separated and the temperature rose to 134° C. during this step. The solution was cooled to 40° C., neutralized with 13 gm of a 40% aqueous potassium carbonate solution and distilled under vacuum. 440 gm of 1,3-dioxa-2-isopropyl-cyclohept-5-ene were obtained, 78% of the theoretical yield, with a boiling point of 65° to 85° C. at 27 mbar.

(b) Preparation of
4,6-dioxa-5-isopropyl-tricyclo[7.2.1.0$^{2,8}$]dodec-10-ene 200 gm (1.4 mol) of 1,3-dioxa-2-isopropyl-cyclohept-5-ene were heated to 200° C. in the autoclave, reacted with 93 gm (0.7 mol) of dicyclopentadiene within two hours and then agitated for three hours. The crude product was distilled off under vacuum (30° to 89° C. at 0.133 mbar, 239 gm) and then fractionated. 135 gm of 4,6-dioxa-5-isopropyl-tricyclo[7.2.1.0$^{2,8}$]dodec-10-ene were obtained (47% of the theoretical yield) with a boiling point of 95° C. at 0.8 mbar and a refractive index $n_D^{25} = 1.4890$. The fragrance of the compound was fruity, mushroomlike, earthy, airy with citrus and jasmone note.

The 4,6-dioxa-5-alkyl-tricyclo[7.2.1.0$^{2,8}$]dodec-10-enes listed below were prepared analogous to the process described above. They also are colorless oils or solids.

EXAMPLE 2

4,6-Dioxa-5-methyl-tricyclo[7.2.1.0$^{2,8}$]dodec-10-ene

Melting point: 92° to 93° C.
Odor: Green, cucumber note.

EXAMPLE 3

4,6-Dioxa-5-ethyl-tricyclo[7.2.1.0$^{2,8}$]dodec-10-ene

Melting point: 46° to 65° C.
Odor: Leaf, humus, mushroom note, fresh.

EXAMPLE 4

4,6-Dioxa-5-propyl-tricyclo[7.2.1.0$^{2,8}$]dodec-10-ene

Boiling point: 62° to 68° C. at 0.0013 mbar.
$n_D^{25} = 1.4921$.
Odor: Leaf, humus, mushroom note, fresh.

EXAMPLE 5

| Synthetic Lavender Oil | |
|---|---|
| | Parts by Weight |
| 4,6-dioxa-5-propyl-tricyclo- | |

| Synthetic Lavender Oil | |
|---|---|
| | Parts by Weight |
| [7.2.1.0$^{2,8}$]dodec-10-ene | 100 |
| Lavandine oil, abrialis | 400 |
| Lavandine oil, acetylated | 300 |
| Terpinyl propionate | 50 |
| Linalool | 40 |
| Linalyl isobutyrate | 20 |
| Lavandulol | 20 |
| Ethylamylketone | 15 |
| Neroli | 10 |
| Spike oil | 10 |
| Linalyl valerate | 5 |
| Cumarin | 5 |
| Citronellol/citronellyl acetate | 5 |
| Geraniol/geranyl acetate | 5 |
| Linalool oxide | 5 |
| n-Hexyl alcohol | 3 |
| 1-Octen-3-ol acetate | 3 |
| Cumin alcohol | 1 |
| Eugenol | 1 |
| Methylheptenone | 1 |
| Hexen-2-al (1) 10% | 1 |
| | 1,000 parts by weight |

EXAMPLE 6

| Fragrance for Soap | |
|---|---|
| | Parts by Weight |
| 4,6-Dioxa-5-isopropyl-tricyclo-[7.2.1.0$^{2,8}$]dodec-10-ene | 155 |
| Boisambrene ®, Henkel | 230 |
| Citronellol | 150 |
| Geraniol | 140 |
| Hydroxycitronellol | 80 |
| α-Amylcinnamaldehyde | 60 |
| Phenylacetaldehyde, 50% in DEP | 50 |
| Vetisclaron ®, Henkel | 60 |
| Isogeranyl nitrile | 30 |
| Phenylethyl alcohol | 30 |
| Benzyl acetate | 10 |
| Nonylaldehyde | 5 |
| | 1,000 parts by weight |

The above formulation is employed in amounts of 0.1% to 2% in hand soap formulations as an odorant.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A perfumery composition comprising from about 1 to 50 percent by weight of at least one tricyclododecene of the formula:

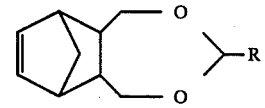

wherein R is a member selected from the group consisting of alkyl having from 1 to 8 carbon atoms, alkenyl having from 2 to 8 carbon atoms and alkynyl having from 2 to 8 carbon atoms, and the remainder customary constituents of perfumery compositions.

2. The perfume composition of claim 1 wherein said customary constituents of perfumery composition include at least one other perfume.

3. The perfume composition of claim 1 wherein R is isopropyl.

4. The method of imparting a desired aroma to a product which comprises administering an aroma-imparting amount of the perfume composition of claim 1.

5. The perfume composition of claim 1 wherein R is selected from the group consisting of methyl, ethyl, propyl and isopropyl.